United States Patent [19]
Kasper

[11] Patent Number: 5,801,354
[45] Date of Patent: Sep. 1, 1998

[54] DEVICE FOR STERILIZING THE INNER SURFACES OF PRESSURE SENSITIVE CONTAINERS

[75] Inventor: Wolfgang Kasper, Altusried, Germany

[73] Assignee: Ruediger Haaga GmbH, Germany

[21] Appl. No.: 827,494

[22] Filed: Mar. 28, 1997

[30] Foreign Application Priority Data

Apr. 20, 1996 [DE] Germany .................. 196 15 735.8

[51] Int. Cl.⁶ .................................................. B23K 10/00
[52] U.S. Cl. .......................... 219/121.43; 219/121.48; 219/121.52; 422/23; 422/906
[58] Field of Search .................. 219/121.43, 121.44, 219/121.52, 121.59, 121.48; 156/345; 422/906, 907, 22, 23

[56] References Cited

U.S. PATENT DOCUMENTS

| | | | |
|---|---|---|---|
| 3,701,628 | 10/1972 | Ashman et al. | 21/54 R |
| 5,262,125 | 11/1993 | Goodman | 422/23 |
| 5,451,368 | 9/1995 | Jacob | 422/23 |
| 5,641,423 | 6/1997 | Bridges et al. | 219/770 |
| 5,650,693 | 7/1997 | Campbell et al. | 315/111.21 |

FOREIGN PATENT DOCUMENTS

| | | |
|---|---|---|
| 2 106 736 | 9/1971 | Germany . |
| 44 08 301 A1 | 9/1994 | Germany . |

*Primary Examiner*—Mark H. Paschall
*Attorney, Agent, or Firm*—Evenson, McKeown, Edwards & Lenahan, P.L.L.C.

[57] ABSTRACT

A device for sterilizing the inner surfaces of pressure sensitive containers with ionized particles has an evacuable chamber which takes up the containers. The electrodes allocated to a container and charged by an alternating voltage, are arranged outside of but closely surround the respective container. The container is subject to equal pressure from the inside and the outside, and the inner surface of the container to be sterilized is also essentially the plasma-limiting wall.

10 Claims, 3 Drawing Sheets

5,801,354

DEVICE FOR STERILIZING THE INNER SURFACES OF PRESSURE SENSITIVE CONTAINERS

BACKGROUND AND SUMMARY OF THE INVENTION

The present invention relates to a device for ion-particle sterilization of the inner surfaces of electrically non-conducting, pressure sensitive containers comprising an unsealed filling opening. The device comprises an evacuable chamber for taking up the containers, a gas supply line connected to the chamber, electrodes for generating a plasma located in the chamber with two electrodes allocated to each container, and an alternating current generator for charging the electrodes with an alternating voltage.

DE 44 08 301 A1 discloses a device in which the containers to be sterilized run through three vacuum chambers, of which the middle one is provided for sterilization treatment of the pressure sensitive containers by low temperature plasma. An electrode pole and a gas nozzle are inserted into each container which stands on a metallic pallet.

The sterilizing effect of a plasma is due to a mechanical as well as a chemical destruction of germs by ion bombardment. Even by applying a very low energy level, the plasma can penetrate into the smallest surface cracks and holes, whereby with increasing vacuum the temperature is reduced to such an extent that even heat sensitive containers can be treated. One disadvantage of the known device lies in the insufficient homogeneity of the plasma which comes into contact not only with the surfaces to be sterilized but also with the remaining surfaces. As a result, a sterilization time of two minutes is necessary for a sufficient sterilization quotient is reached. A sterilization time of this length is too long for industrial application.

German published patent application 21 06 736 discloses sterilizing the inner surfaces of a container with a low pressure plasma based on chlorine, bromine or iodine. In one embodiment, the containers are arranged inside a reactor which is surrounded by a coil. In another embodiment, the containers are treated in the inside of a reactor, whereby an electrode is arranged in the container and a second electrode surrounds the container. In a third embodiment, the container is also the reactor and is surrounded directly by a coil. One disadvantage is that in the first two embodiments, the containers are hit by the plasma from the outside, so that the plasma is not particularly effective in the Interior of the container. In the latter embodiment, only pressure insensitive containers can be sterilized, as the vacuum occurs only on the inside of the container.

It is an object of the present invention to sterilize the inner surfaces of pressure sensitive containers with a device in which the surface to be sterilized is essentially also the plasma-limiting wall.

This object has been achieved in accordance with the present invention by arranging both electrodes outside of the respective container while closely surrounding same.

As a result of the arrangement of the electrodes according to the present invention, it is ensured, on one hand, that the same low pressure prevails inside and outside the container, while on the other hand the surface to be sterilized is also essentially the plasma-limiting wall, which results in a high degree of effectiveness of the plasma and a short sterilization time. With this capacitive excitation, the ions hit the untreated wall at a particularly high energy level, which results in a high sterilization quotient which reaches at least $10^4$. This sterilization quotient is defined as follows:

$$SQ = a/b$$

The letter a denotes the quantity of germs before sterilization, while b denotes the quantity of germs after sterilization.

When the two electrodes closely surround the container by the two electrodes in the manner according to the present invention, a small gap is created. This gap permits the vacuum there to become effective, but which, however, due to its small dimensions, prevents a plasma being activated already outside of the container, that is, there where it is not required. The size of the gap is determined by the so-called Debye length, which sets the characteristic shielding length and which measures between 100 und 500 µm in practical use of the present invention. Thus a great homogeneity is reached on the actual surfaces to be sterilized, so that sterilization times of only a few seconds become possible. The effective vacuum on the inside and outside of the container permits on the one hand pressure sensitive containers to be sterilized, while on the other hand, due to the high vacuum, the sterilizing temperatures are so low that even heat sensitive containers, for example, paper containers, can be treated.

In connection with the present invention, "pressure sensitive" containers here include not only compressible containers, for example those made of paper, but also containers which only sporadically break under pressure, for example, glass bottles.

The electrodes can be positioned to the container from two sides. This positioning makes it possible not only to apply the electrodes according to the present invention so that they surround the container, but also to adjust the necessary small gap in a simple manner so that the electrodes are guided practically to the point of contact on the outer wall of the container. The vacuum necessary for the outside of the container is hereby not affected.

At least one electrode can advantageously be arranged to a plurality of containers. This results in a reduction of installations per container. Thus, for example, a longer container row can be arranged between, in all, only two electrodes.

In one embodiment of the present invention, the electrodes have a recess in the area bordering directly on the filling opening. Thus the outer area of the container directly adjoining the filling opening is also sterilized. This is particularly advantageous when the recess is also the receiver for a sealing piece arranged to the filling opening. This sealing piece can be, for example, a so-called pull-tab, which is already applied adjacent to the filling opening on the lid of the container. Container and sealing piece need not then be separately In sterilized.

One particular advantage of the present invention lies therein that the evacuable volume of the chamber consists essentially only of the inside of the containers. Due to the practical arrangement of the electrodes and the wall of the container—surrounding chamber, the space of the chamber to be evacuated, insofar as it is located outside of the containers, can be kept very small. Although the containers are surrounded by an evacuable chamber, the practical effect is similar as when the containers themselves formed the reactor. Thus only a small amount of air needs to be pumped out.

For the purpose of the present invention, the chamber is subject to an operational pressure of 1 to 100 Pa. This low pressure has a resultant low gas temperature, as is necessary for example for paper cans. The low operational pressure results further in reducing the sterilization time to a few seconds.

Non-toxic gases are chosen for the purpose of the present invention, whereby oxygen, hydrogen, nitrogen, helium, neon, argon, krypton, steam, hydrogen peroxide steam or mixtures of these gases are preferably contemplated. It has proved, however, particularly advantageous to use hydrogen or helium for ionization. These gases form the lightest and smallest possible ions in the plasma. The ions can penetrate into the smallest pores of the container and diffuse most efficiently towards the surface at a high ionization energy level.

For the purpose of the present invention, a high frequency is provided for the alternating voltage, which frequency lies between the plasma frequencies of the ions and the electrons. Thus the permissible high frequency of 13.56 Mhz is applied.

In a particularly advantageous currently contemplated embodiment of the present invention, the chamber is configured as a so-called parallel plate reactor. Thus a great number of containers can be sterilized at the same time in a particularly cost-effective way. If, for example, twenty containers are sterilized at the same time in a sterilization time of 16 seconds, the cycle time per container is reduced in this way to under one second.

BRIEF DESCRIPTION OF THE DRAWINGS

These and further objects, features and advantages of the present invention will become more readily apparent from the following detailed description thereof when taken in conjunction with the accompanying drawings wherein.

DETAILED DESCRIPTION OF THE DRAWINGS

Figure 1:
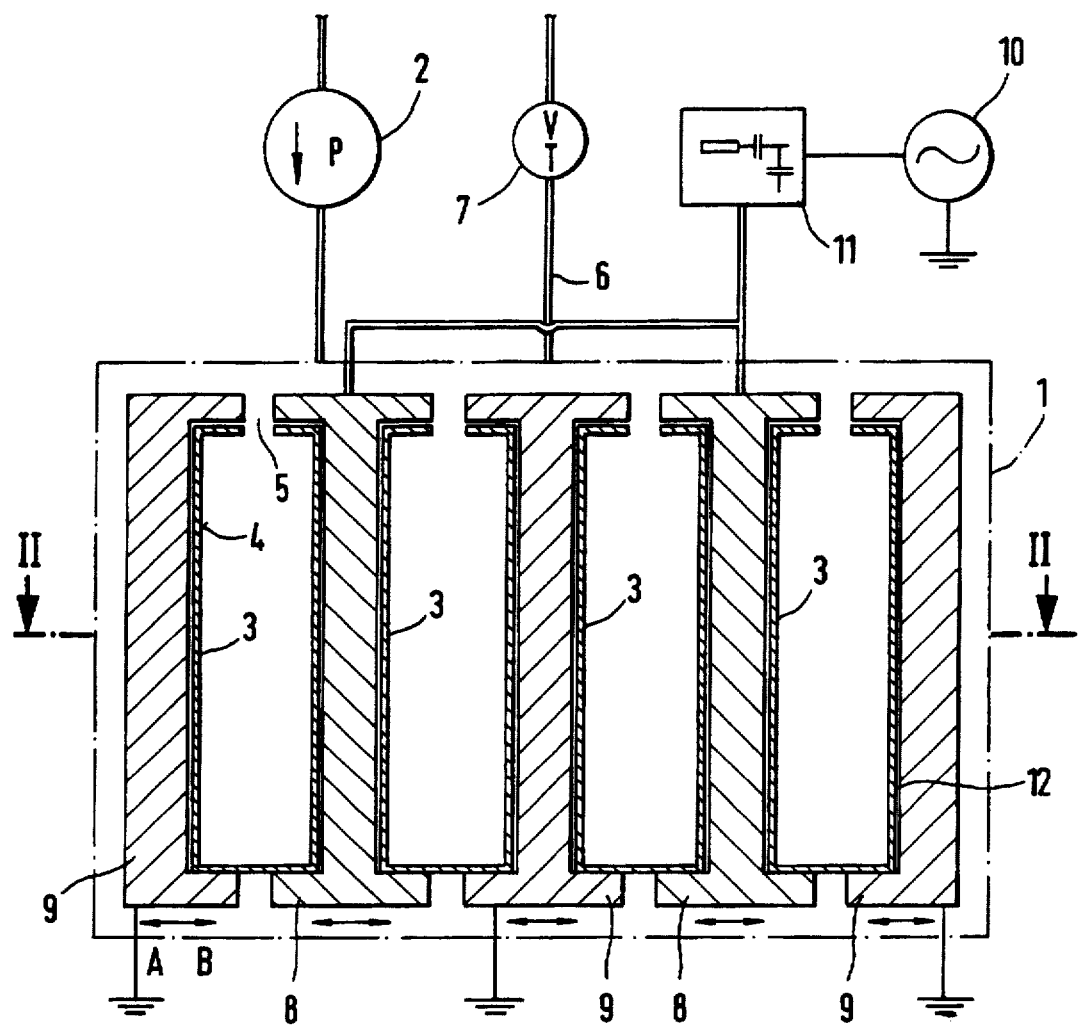
FIG. 1 is a side, cross-sectional view of a device an accordance with the present invention, in which a parallel plate reactor sterilizes pressure sensitive containers.

Referring now to the drawings, an evacuable chamber 1 is denoted only by a dot-dash contour or outline. The chamber 1 is formed so that, as is known with various types of reactors, containers 3 which are to be sterilized can be inserted into the chamber 1 after it has been opened, whereby the chamber 1 must be subsequently sealed closed. For the purpose of carrying out the invention, the chamber 1 is arranged to a transport device (not shown) which, for example, feeds the containers 3 from above, inserts them into the chamber 1, and removes the containers 3 from the chamber 1 from below. For this process, the evacuable chamber 1, which must be sealed against the outside during operation, is configured to be easily opened and closed in a manner generally well known. The chamber 1 can be evacuated by a vacuum pump 2 to a low pressure of 1 to approximately 100 Pa.

The chamber 1 serves to simultaneously receive a plurality of containers 3, for example 20, whose inner surfaces 4 are to be sterilized. In particular, containers 3 which do not conduct electricity and which are also pressure sensitive are also contemplated, for example paper containers 3. Each of these containers 3 has a filling opening 5, which is not sealed during sterilization. After sterilization, a filling substance can be poured through the filling opening 5, after which the filling opening 5 is sealed.

Figure 2:
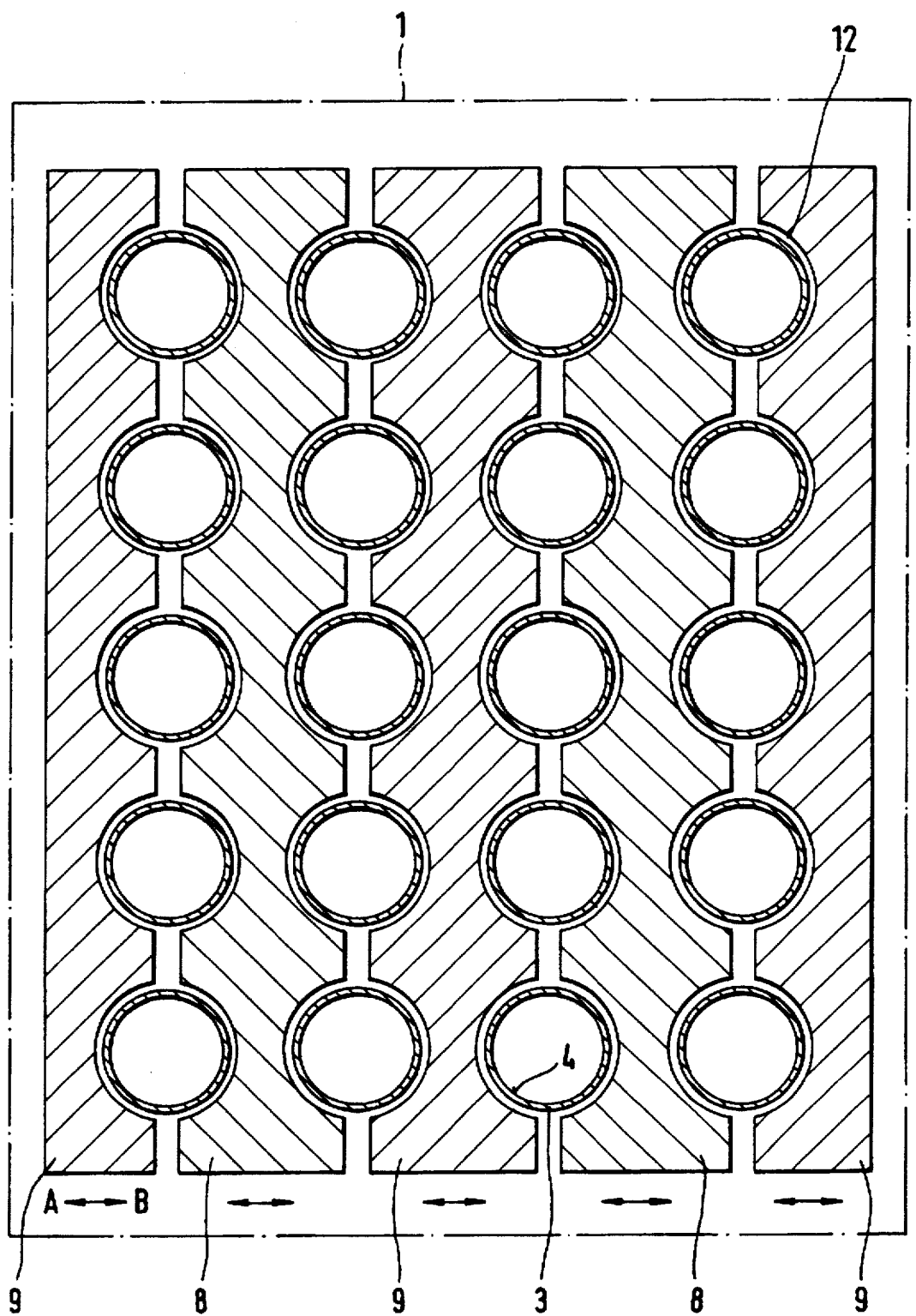
FIG. 2 is a cross sectional view along line II—II of FIG. 1.

As can be seen in particular from FIG. 2, the containers 3 which are to be sterilized are arranged adjacent to one another in a plurality of rows inside the chamber 1. A supply line for the ionization gas, for example hydrogen, is connected to the chamber 1 and the flow of this gas can be regulated by a choker valve 7 as seen in FIG. 1.

A plurality of electrodes 8, 9 are inside the chamber 1 and extend parallel to the rows of containers 3. The electrodes 8 are connected to an alternating voltage and the electrodes 9 are grounded. Although each of these electrodes 8, 9 are arranged to a plurality of containers 3, two electrodes 8, 9 are provided for each container 3. The chamber 1 is formed (not shown) so that the electrodes 8, 9 can be adjusted relative to one another in accordance with the directions of arrow A and B in a generally known manner in order that the containers 3 can be inserted unimpeded into the chamber 1, whereafter the electrodes 8, 9 are placed to the respective containers 3 from two sides.

The contour of the electrodes 8, 9 is configured to the outer contour of the containers 3 so that the electrodes 8, 9 can closely surround the containers 3 practically without leaving a gap. For example, the containers 3 can be cylindrical in form. Other contours are, however, possible, for example, standard bottle forms, and the cylindrical contour is to be taken as merely exemplary here.

The electrodes 8 are connected to a high frequency alternating current generator 10 via an intermediate, a so-called matchbox 11 which transmits the alternating voltage from the alternating current generator 10 into the plasma to be activated. The matchbox 11 serves to adapt the impedance of the plasma to the alternating current generator 10.

After placement of the electrodes 8, 9 laterally on the containers 3, a narrow gap 12 arises on each side. This gap 12 enables the vacuum, generated by the vacuum pump 2, to form not only in the inside of the containers 3 but also around the containers 3. Such vacuum formation is absolutely vital for pressure sensitive containers 3. The gap 12 should, however, be sufficiently narrow as to be smaller than the Debye length mentioned above, so that plasma cannot form outside of the containers 3, that is between the electrodes 8,9 and the outer walls of the containers 3. Rather, the plasma should be practically only activated inside the containers 3, i.e., the location of the inner surfaces 4 to be sterilized. Due to the arrangement of the electrodes 8, 9 which are arranged outside of the containers 3 but also closely surround the containers 3, the same vacuum now prevails both inside and outside the containers 3, and practically only the inner surfaces 4 of the containers 3 form the plasmalimiting wall. Together with the predetermined vacuum, this arrangement results in sufficiently short sterilization times.

Figure 3:
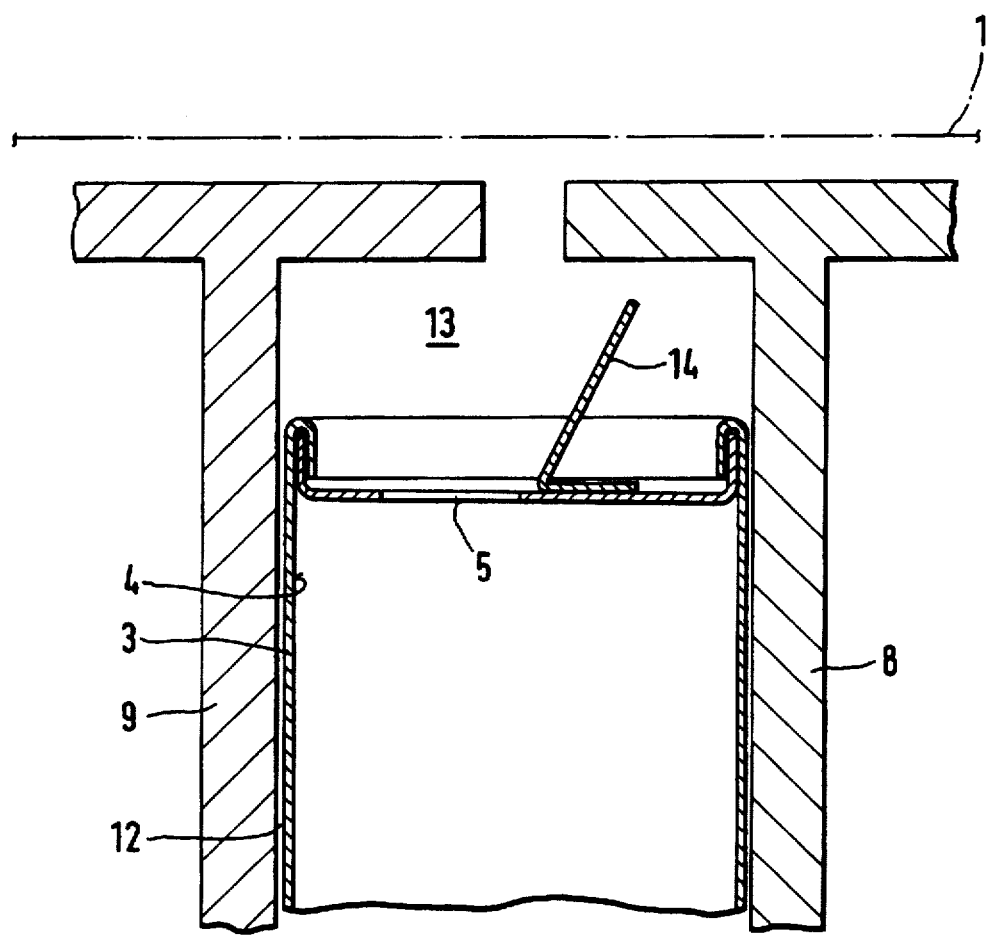
FIG. 3 is an enlarged drawing of a detail from FIG. 1 in the area of a filling opening of the container to be sterilized.

In contrast to FIG. 1, the electrodes 8, 9 shown enlarged in FIG. 3, form a small recess 13, which means that, in the area of the filling opening 5, a plasma can also be activated outside the container 3. This is particularly advantageous when a sealing piece 14, for example a so-called pull tab, is arranged at the filling opening 5, which is then simultaneously sterilized.

After plasma sterilization, when the inside of the chamber 1 is subjected to a normal pressure again, the containers 3 can be filled with a filling substance while they are still inside the chamber 1. For this purpose, a conventional filling nozzle (not shown) is inserted into the chamber 1. Consequently the containers 3 are sterilized, filled and sealed inside the chamber 1.

The electrodes 8, 9, together with the wall of the chamber 1, can be so arranged that the evacuable volume of the chamber 1 consists essentially only of the inside of the containers 3, so that only a small amount of air has to be pumped out for the purposes of sterilization. During sterilization, the chamber 1 is subjected to an operational pressure which can be regulated at between 1 and 100 Pa. This results in a sufficiently low gas temperature which lies only slightly above room temperature.

In order that preferably light ions with high ionization energy are produced, hydrogen or helium are the first choices of a gas. A high frequency of, for example, 13.56 Mhz is provided for the alternating voltage to charge the electrodes 8, 9.

As can be seen in particular in FIG. 2, the evacuable chamber 1 is configured as a parallel plate reactor. The electrodes 8, 9 are placed to the containers 3 in accordance with the arrow directions A and B. The length of the electrodes 8, 9 corresponds hereby to the length of a row of containers 3.

Although the invention has been described and illustrated in detail, it is to be clearly understood that the same is by way of illustration and example, and is not to be taken by way of limitation. The spirit and scope of the present invention are to be limited only by the terms of the appended claims.

I claim:

1. A device for sterilization with ionized particles inner surfaces of electrically non-conducting, pressure sensitive containers having an unsealed filling opening, comprising an evacuable chamber for receiving the containers, a gas supply line attached to the chamber, plasma-generating electrodes located in the chamber two electrodes for each container, and an alternating current generator for supplying an alternating voltage to the electrodes, wherein both electrodes are arranged outside of and defining a Debye length determined cap surrounding an outer surface of the associated container.

2. The device according to claim 1, wherein the electrodes can be arranged from two sides of the container.

3. The device according to claim 1, wherein at least one electrode is associated with a plurality of the containers.

4. The device according to claim 1, wherein the electrodes comprise a recess in the area directly adjacent the filling opening.

5. The device according to claim 4, wherein the recess is configured to receive a sealing piece at the filling opening.

6. The device according to claim 1, wherein the evacuable volume of the chamber consists essentially of the inside of the containers.

7. The device according to claim 1, wherein the chamber is arranged to be subjected to an operational pressure of 1 to 100 Pa.

8. The device according to claim 1, wherein one of hydrogen gas and helium gas is a source for the ionized particles.

9. The device according to claim 1, wherein the alternating voltage has a frequency of 13.56 Mhz.

10. The device according to claim 1, wherein the chamber is a parallel plate reactor.

* * * * *